United States Patent [19]

Crittenden et al.

[11] Patent Number: 4,988,356
[45] Date of Patent: Jan. 29, 1991

[54] CATHETER AND GUIDEWIRE EXCHANGE SYSTEM

[75] Inventors: James F. Crittenden, Hollis, N.H.; Michael D. Barbere, Dunstable; Bryan J. White, Lowell, both of Mass.

[73] Assignee: C. R. Bard, Inc., Murray Hill, N.J.

[21] Appl. No.: 185,796

[22] Filed: Apr. 25, 1988

Related U.S. Application Data

[63] Continuation of Ser. No. 19,644, Feb. 27, 1987, abandoned.

[51] Int. Cl.5 .............................................. A61M 29/00
[52] U.S. Cl. ................................... 606/192; 606/194; 604/160; 604/96
[58] Field of Search ............... 128/344, 348.1, 325; 604/96, 102, 110, 111, 160, 161; 606/192-197

[56] References Cited

U.S. PATENT DOCUMENTS

| Re. 31,855 | 3/1985 | Osborne | 604/161 |
|---|---|---|---|
| 3,262,449 | 7/1966 | Pannier, Jr. et al. | 604/162 |
| 3,297,030 | 1/1967 | Czorny et al. | 604/160 |
| 3,550,591 | 12/1970 | MacGregor | 604/161 |
| 3,682,173 | 8/1972 | Center | 604/160 |
| 3,853,130 | 12/1974 | Sheridan | 128/349 R |
| 4,175,564 | 11/1979 | Kwak | 128/350 R |
| 4,411,654 | 10/1983 | Boarini et al. | 604/161 |
| 4,569,347 | 2/1986 | Frisbie | 604/165 |
| 4,573,470 | 3/1986 | Samson et al. | 128/344 |
| 4,585,013 | 4/1986 | Harris | 604/160 |
| 4,619,644 | 10/1986 | Scott | 604/160 |
| 4,748,982 | 6/1988 | Horzewski et al. | 604/160 |
| 4,762,129 | 8/1988 | Bonzel | 128/344 |
| 4,771,777 | 9/1988 | Horzewski et al. | 128/344 |

FOREIGN PATENT DOCUMENTS

82/03558 10/1982 PCT Int'l Appl. ............. 128/348.1
2127294 4/1984 United Kingdom .

Primary Examiner—C. Fred Rosenbaum
Assistant Examiner—Kathleen A. Daley
Attorney, Agent, or Firm—Wolf, Greenfield & Sacks

[57] ABSTRACT

A catheter and guidewire exchange system in which the guideware is contained within a guidewire leumen in the indwelling portion of the catheter and with the guidewire and catheter being separated externally of the patient. The catheter includes a guidewire lumen which is slit longitudinally along the length of the catheter. The guide member is carried by the catheter and serves to spread the slit of the lumen to guide the guidewire into or out of the slit guidewire lumen. The guide member may be advanced along the catheter and guidewire in zipper-like fashion so that the proximal ends of the guidewire and catheter will be separated while the distal portions will be merged.

27 Claims, 3 Drawing Sheets

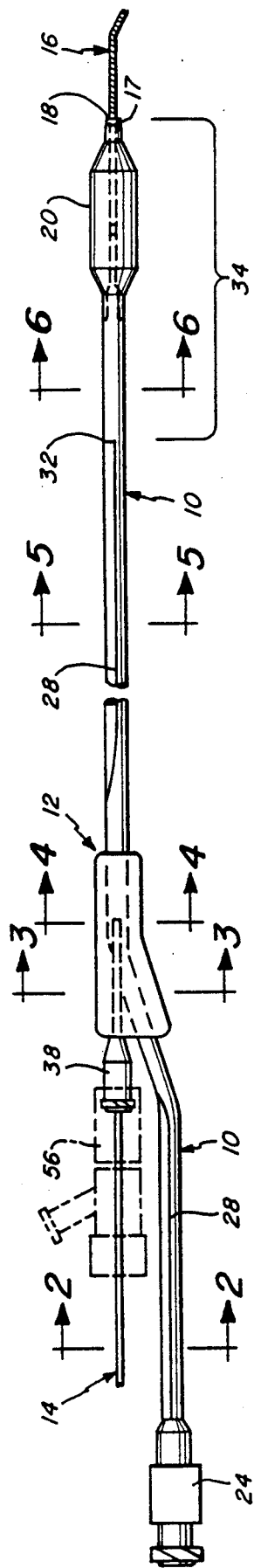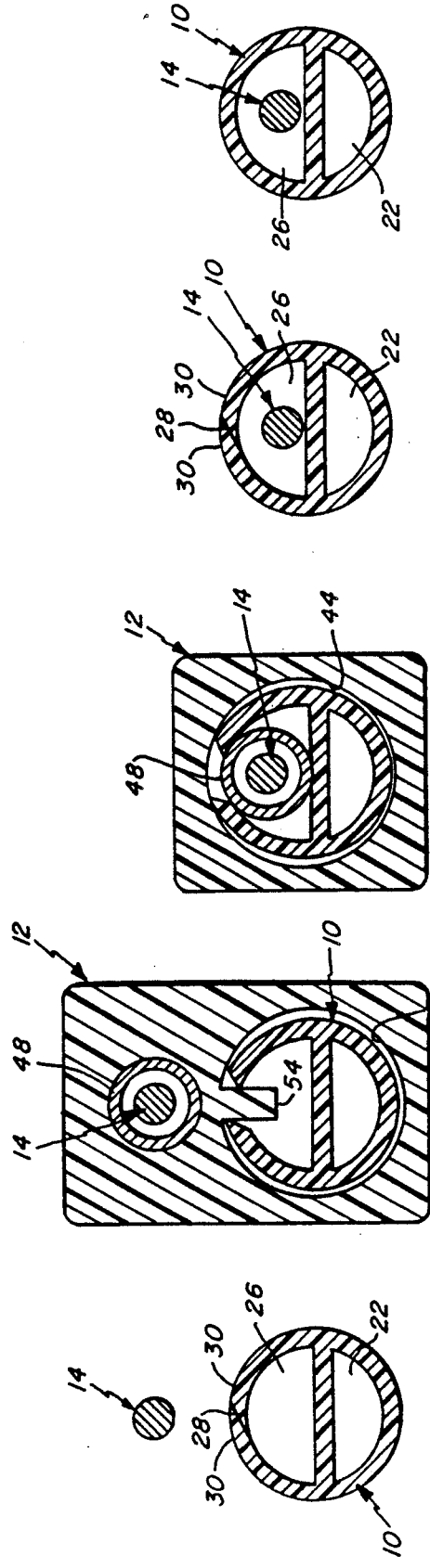

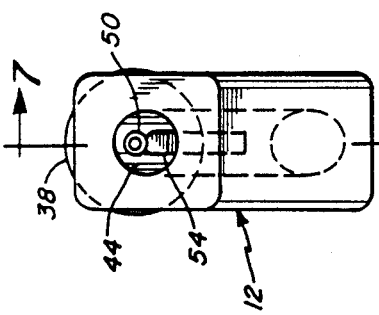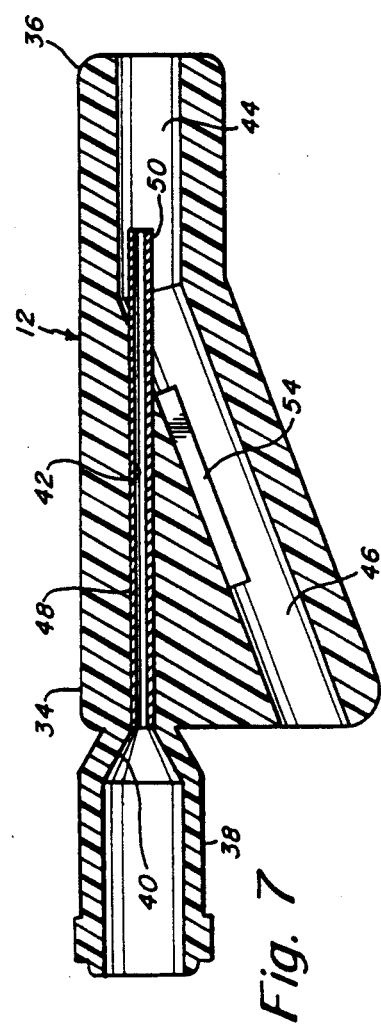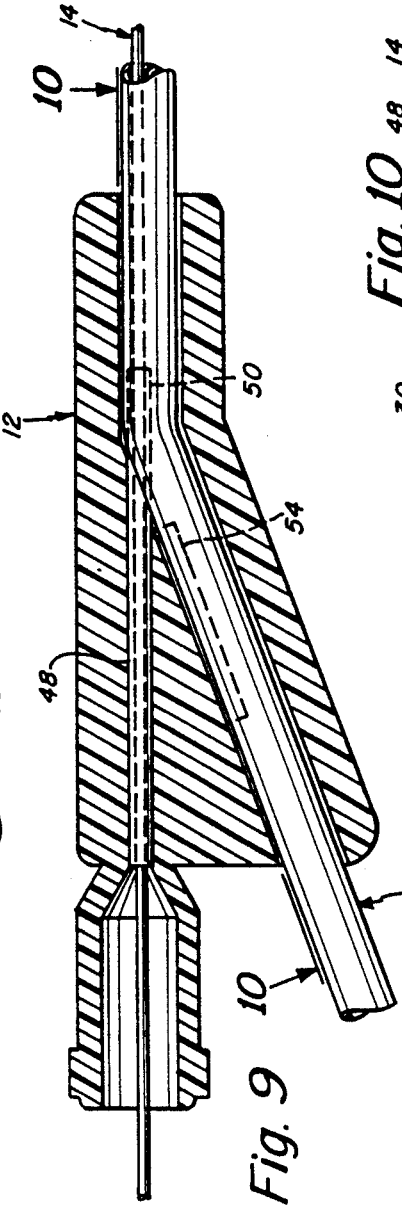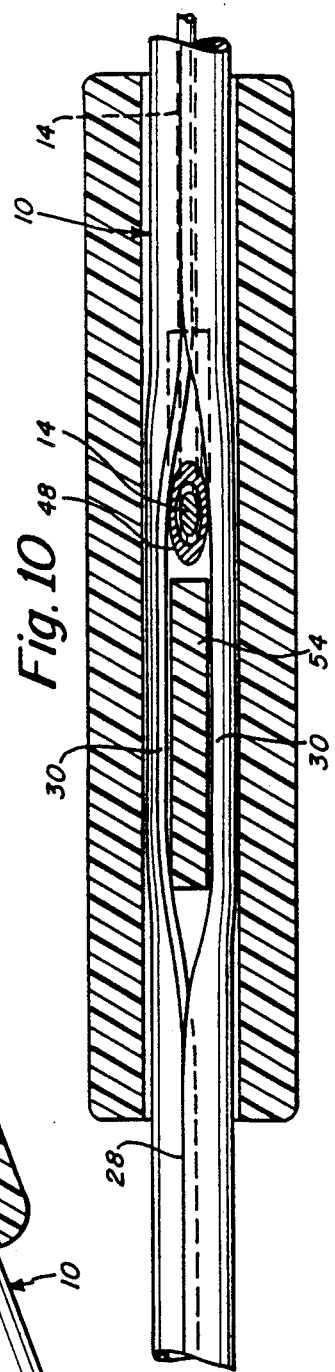

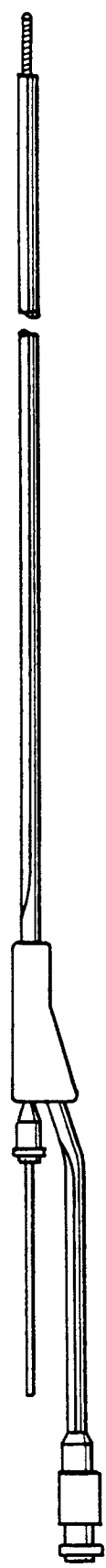
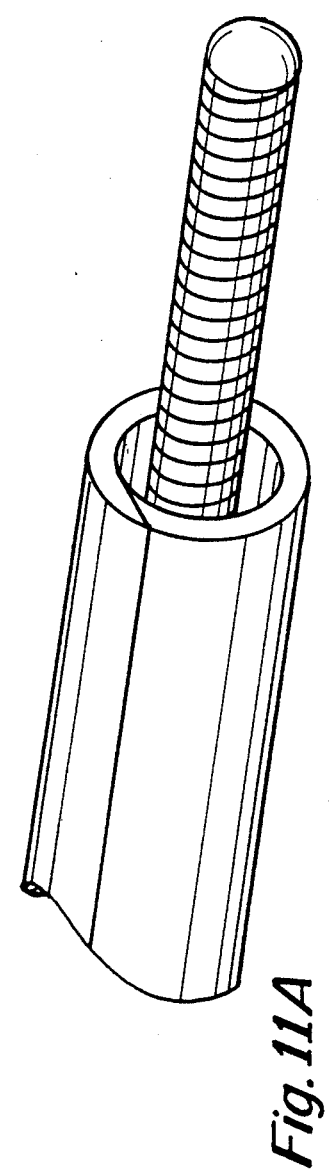
Fig. 11
Fig. 11A
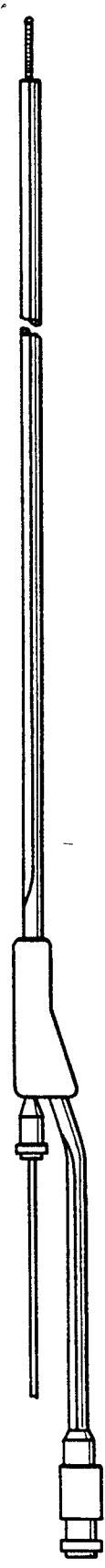
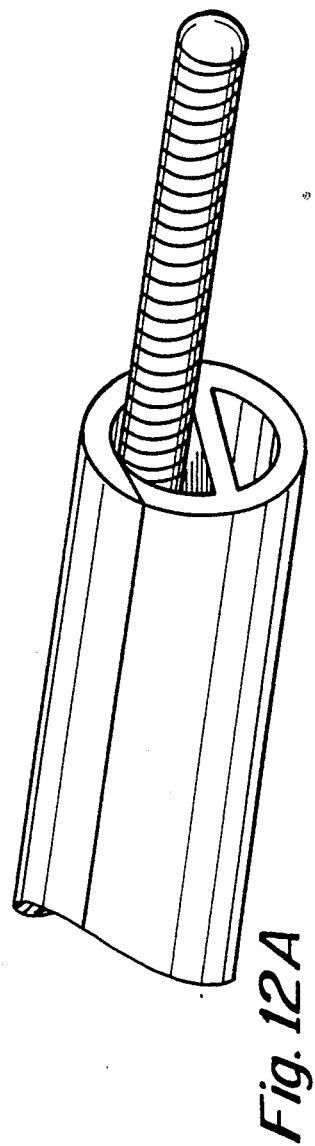
Fig. 12
Fig. 12A

CATHETER AND GUIDEWIRE EXCHANGE SYSTEM

This application is a continuation of application Ser. No. 019,644, filed 2/27/87 now abandoned.

FIELD OF THE INVENTION

This invention relates to catheters placed in the body of a patient such as in the cardiovascular system and, in particular, to a system for facilitating exchange of such catheters and for transporting such catheters to selected sites within the patient.

BACKGROUND OF THE INVENTION

Catheters are placed at various locations within a patient for a wide variety of purposes and medical procedures. For example only, one type of catheter is a balloon dilation catheter which is used in the treatment of a vascular stenosis. Such a catheter has a balloon at its distal end which is intended to be placed, in a deflated condition, within the stenosis, and then inflated while in the stenosis to expand radially the stenosed lumen of the blood vessel. Typically, the placement of such catheters involves the use of a guidewire which may be advanced through the patient's vasculature to the location which is to be treated. The catheter, which has a lumen adapted to receive the guidewire, then is advanced over the wire, or the wire and the catheter may be advanced in unison with the wire protruding from the distal end of the catheter. In either case, the wire serves to guide the catheter to the location to be treated.

It often becomes necessary, in the performance of a catheter procedure, to exchange the indwelling catheter for another catheter, for example, for a catheter having a different size balloon. In a typical catheter exchange, the guidewire first is removed from the lumen of the indwelling catheter. Then a longer exchange wire, usually about twice the length of the catheter, is passed through the catheter to replace the original wire. Then, while holding the exchange wire by its proximal end to maintain it in place, the catheter is withdrawn proximally from the blood vessel over the exchange wire. After the first catheter has been removed, the next catheter then is threaded onto the proximal end of the exchange wire and is advanced along the exchange wire and through the patient's blood vessels until the distal end of the catheter is located as desired. The exchange wire may be permitted to remain in place or may be exchanged for a shorter, conventional length guidewire.

A device, referred to as the "monorail" system, has been proposed recently which would modify the foregoing catheter exchange technique. In the proposed monorail system, the catheter is formed so that the guidewire is located outside of the catheter except for a short segment at the distal end of the catheter, which passes over the wire. The distal segment of the catheter has a short lumen which extends from the distal tip of the catheter to a more proximally located opening near the distal tip. In use, the guidewire is placed initially in the patient's vascular system. The distal segment of the catheter then is threaded onto the wire. The catheter can be advanced alongside the wire with its distal segment being attached to and guided along the wire. The catheter can be removed and exchanged for another catheter without the use of the usual double length exchange wire and without requiring withdrawal of the initially placed guidewire.

Although the proposed monorail catheter system may avoid the requirement for using a long exchange wire, it presents several difficulties. For example, it is not possible to exchange guidewires in an indwelling catheter, should that be desired. Additionally, the device presents a potential for damaging the delicate inner surface of an artery from a tension load applied to the guidewire which would tend to straighten the artery. Also, there is an increased risk of guidewire entanglement in those procedures where multiple guidewires are used, because the guidewires are exposed within the blood vessel. It is among the general objects of the invention to provide an improved device which overcomes the foregoing difficulties.

SUMMARY OF THE INVENTION

In accordance with the invention, a catheter is provided with a guidewire lumen formed through the elongate body of the catheter. The guidewire lumen is constructed to receive and retain the guidewire fully within and along the indwelling length of the catheter but enables the guidewire to extend out of the guidewire lumen for most of the proximal portion of the catheter which is exposed externally of the patient. The guidewire lumen extends along the length of the catheter, from its proximal end to its distal end. The catheter body is slit longitudinally along the guidewire lumen. The slit enables the guidewire to extend transversely into or out of the lumen through the slit, and at any location along the length of the slit. The slit may extend the full length of the catheter, to the distal tip of the catheter except in those catheters which have an encircling member at the distal tip, such as a balloon, in which case the slit terminates proximally of the encircling member, thus leaving a short unslit distal segment. The system of the present invention includes a guiding device which is slidably carried by the catheter and which serves to merge or to separate the guidewire and catheter lumen at any location along the length of the guidewire or catheter. The guide device has two proximal inlet passageways which merge into a common distal outlet. The inlets receive the separate guidewire and catheter which exit from the common outlet in a merged form in which the guidewire is disposed within the lumen of the catheter. The relative direction of movement of the catheter, guidewire and guide device determine whether the guiding device merges or separates the catheter and the wire.

When using the system, the guidewire first is placed in the patient's vascular system with the distal end of the guidewire placed at the desired location in the patient's blood vessel. The catheter is threaded onto the guidewire which passes through the guidewire lumen until the proximal end of the guidewire enters the guide device where it is guided transversely through the slit in the catheter and out of the guidewire lumen of the catheter. The guide device is constructed to engage and spread the slit in the catheter body while guiding the guidewire out of the guidewire lumen. The catheter may be advanced into the patient by securing the position of the guidewire relative to the guiding device and advancing the catheter through the guiding device which spreads the slit and guides the catheter so that the guidewire lumen wraps about and embraces the guidewire. The catheter and guidewire exit from the common branch of the guide device with the guidewire in the lumen. In reverse operation, when the catheter is withdrawn, the guide device separates the catheter and guidewire to enable either the guidewire or the catheter to be withdrawn independently through its respective branch in the guide device. In another mode of operation, the guide device may be operated as a zipper by holding the catheter and guidewire stationary and by advancing the guide device either in a distal direction to separate the wire and catheter or in a proximal direction to merge them together. The wire thus is enclosed within the catheter lumen along the full length of the indwelling portion of the catheter. Thus, it is possible to remove the guidewire and replace it with another wire if desired without removing the catheter from the patient. Except for the distal end of the guidewire, which protrudes out of the distal tip of the catheter, the guidewire is covered at all times while within the blood vessel, thus reducing the risk of injury to the blood vessel intima as well as the risk of wire entanglement in multiple wire procedures.

It is among the objects of the invention to provide an improved catheter and guidewire system.

Another object of the invention is to provide a guidewire and catheter system in which the portion of the guidewire which extends along the indwelling portion of the catheter is contained within the catheter but in which the externally disposed portion of the catheter does not contain the guidewire.

A further object of the invention is to provide a device of the type described which enables guidewire exchanges to be made through the indwelling catheter.

A further object of the invention is to provide a device of the type described which enables catheter exchanges to be made without using exchange wires.

Another object of the invention is to provide a system of the type described in which the guidewire resides in the indwelling portion of the catheter and separates from the catheter externally of the patient to provide a grippable portion for the physician.

A further object of the invention is to provide a system of the type described in which the guidewire exits transversely of the catheter through a slit formed in the catheter wall.

BRIEF DESCRIPTION OF THE DRAWINGS

The foregoing and other objects and advantages of the invention will be appreciated more fully from the following further description thereof with reference to the accompanying drawings.

FIG. 1 is an illustration of one embodiment of the catheter, guidewire and guide member of the invention in an assembled configuration;

FIG. 2 is a sectional illustration of the catheter and guidewire as seen along the line 2—2 of FIG. 1;

FIG. 3 is a sectional illustration of the catheter, guidewire and guide member as seen along the line 3—3 of FIG. 1;

FIG. 4 is a sectional illustration of the catheter, guide member and guidewire as seen along the line 4—4 of FIG. 1;

FIG. 5 is a sectional illustration of the catheter and guidewire as seen along the line 5—5 of FIG. 1;

FIG. 6 is a sectional illustration of the catheter and guidewire as seen along the line 6—6 of FIG. 1;

FIG. 7 is an enlarged sectional illustration of the guide member as seen along the line 7—7 of FIG. 8;

FIG. 8 is an end view of the distal end of the guide member;

FIG. 9 is an illustration of the guide member with the guidewire and catheter extending therethrough and illustrating the manner in which the guide member merges the guidewire and catheter;

FIG. 10 is an illustration of the juncture region of the guide member with the guidewire and catheter in place as seen along the line 10—10 of FIG. 9;

FIG. 11 and FIG. 11A is a broken and partially enlarged illustration of an embodiment of the invention in which the slit in the guidewire lumen extends fully to the distal tip of the catheter; and FIG. 12 and FIG. 12A is a broken and partially enlarged illustration of a two lumen catheter in which the slit in the guidewire lumen extends to the distal tip and in which at least one additional, unslit lumen is provided.

DESCRIPTION OF THE PREFERRED EMBODIMENT

As shown in FIG. 1, the invention includes a catheter, indicated generally by the reference character 10 on which a guide member 12 is slidably mounted. A guidewire 14 is illustrated as extending through the guide member 12. The guide member 12 serves as a juncture in which the catheter 10 and guidewire 14 may be merged or separated so that the portion of the guidewire which extends proximally of the guide member 12 (to the left as seen in FIG. 1) is separated from the catheter 10 and the portion of the guidewire 14 which is located distally of the guide member 12 (to the right as seen in FIG. 1) is contained and housed within the catheter 10 except for the most distal end 16 of the guidewire 14 which may protrude distally out of a distal outlet opening 18 of the catheter 10.

The catheter 10 includes an elongate, flexible, cylindrical main body which may be formed from an extruded plastic material such as, for example, polyethylene. In the embodiment shown in FIG. 1, the catheter 10 is a balloon dilation catheter used in angioplasty procedures and has a balloon 20 formed near the distal end of the catheter 10 and which encircles the catheter body. The balloon 20 may be inflated and deflated through an inflation lumen 22 formed through the body of the catheter 10. The inflation lumen extends from the proximal end of the catheter, where it communicates with a fitting 24 and extends the length of the catheter, terminating in communication with the interior of the balloon 20. The fitting 24 is intended to be connected to a suitable source of pressurized fluid or suction to inflate or deflate the balloon 20. The catheter 10 includes a second lumen, indicated at 26 which is intended to receive the guidewire 14. The guidewire lumen 26 may extend the full length of the catheter, terminating at the distal outlet 18. The guidewire lumen 26 need not extend completely to the proximal fitting 24, although it may so extend, if desired.

In accordance with the invention, the body of the catheter 10 is formed with a longitudinal slit 28 which, when the catheter 10 is viewed in cross-section (as FIG. 2), may be considered as defining a pair of flaps 30 which normally close together at the slit 28 to define the enclosed guidewire lumen 26. As seen in cross-section in FIG. 2, the slit 28 preferably is formed so that it extends in a generally tangential direction with respect to the generally circular wall of the catheter. The tangentially oriented slit has been found to provide a somewhat better seal and enables fluids at relatively low pressures to flow through the guidewire lumen. This enables the guidewire lumen also to serve as a low pressure in fusion lumen, such as for the infusion of drugs under low pressure and relatively low flow rates. The guidewire lumen 26 may be circular in cross-section or may be non-circular; in either case, the cross-sectional dimensions of the guidewire lumen 26 are greater than the cross-sectional dimension of the guidewire 14 to permit relative longitudinal movement between the guidewire 14 and catheter 10.

The proximal end of the slit 28 may terminate at or near the fitting 24. In the embodiment shown in FIG. 1, in which the catheter has an encircling member, such as the balloon 20, at its distal end, the distal end 32 of the slit 28 terminates short of the distal tip 17 of the catheter, thereby leaving a distal segment 34 of the catheter 10 which is unslit and in which the guidewire lumen 26 is defined by a continuous, unslit surrounding wall as shown in FIG. 6. It should be understood, however, that the principals of the invention also are usable with catheters which do not have encircling members at their distal ends and, in those catheters, the slit 28 may extend fully to the distal tip of the catheter, as desired.

The guide member 12 may be molded from a suitably rigid plastic material such as a polycarbonate (e.g., Lexan). The member 12 may be considered as having a proximal end 34 and a distal end 36. An inlet fitting 38 is formed at the proximal end 34 and may be formed with a tapered passage 40 which, in turn,.leads into a distally extending bore 42. The bore 42 extends toward a larger diameter common passageway 44 which exits at the distal end 36 of the member 12. The member 12 also includes a catheter passageway 46 which extends at an oblique angle to the bore 42 and passageway 44 and merges with bore 42 and passageway 44 in the region of their juncture. In the illustrative embodiment, a tubular member 48, which may be formed from hypodermic tubing, is mounted securely within the bore 42 and has a distal end 50 which projects into the common passageway 44, adjacent the juncture with the catheter passageway 46. The tube 48 defines a guidewire passageway 40 and communicates the luer fitting 38 with the common passageway 44. A spreader member 54 is formed in the body of the guide member 12 and projects into the catheter passageway 46, the spreader being disposed adjacent the distal end of the catheter passageway.

The guide member 12 may be formed conveniently in two molded halves, separated along the passageways with the tubular member 48 being placed in the passageways, as shown, when the halves of the device 12 are assembled and adhesively bonded together. When the catheter is of the type having an unslit distal segment, it may be placed in its respective channel during assembly of the guide member 12.

When the catheter 10 and guidewire 14 both pass through the guide member 12, they merge at the juncture of the passageways as indicated in FIGS. 9 and 10. The guidewire 14 extends through the guidewire passageway defined by the tube 48 and into and through the common passageway 44. The catheter 10 extends through the catheter passageway 46 and engages the spreader 54 which extends through the slit 28 in the catheter 10 to spread the flaps 30 apart as indicated in FIG. 10. As the catheter advances distally relative to the guide member 12, it advances to the juncture of the passageways and into the common passageway 44 where the guidewire lumen wraps about the distal end 50 of the tube 48, and the guidewire 14 contained within the distal end 50 as shown in FIG. 3. Thus, when the catheter 10 advances relative to the guide member 12 past the distal end 50 of the tube 48, the guidewire 14 becomes enclosed within the guidewire lumen 26 and the flaps 30 draw together under the influence of the inherent resiliency of the catheter body to close the slit 28 of the catheter. The guidewire is contained within the guidewire lumen from that point to the distal end 17 of the catheter where it may exit through the distal outlet opening 18.

From the foregoing, it will be appreciated that the catheter may be advanced distally relative to the guidewire 14 and guide member 12 so as to cause the catheter to envelop and contain the guidewire 14 completely within the guidewire lumen 26. The guidewire 14 may be advanced distally or withdrawn proximally with respect to the guide member 12 and catheter.

The system may be used by first percutaneously inserting and advancing the guidewire 14 into the patient's blood vessel or other body vessel to be treated so that the distal end 16 of the guidewire 14 is located in the intended place in the patient's vessel. For example only, the invention may be used in connection with steerable guidewires of the type described in U.S. Pat. No. 4,545,390 to Leary. The guidewire lumen of the catheter then may be flushed with saline. The distal end of the catheter then is threaded onto the proximal end of the guidewire which is passed through the guide member 12 so that the proximal member of the guidewire 14 protrudes out of the inlet 38. As illustrated in phantom in FIG. 1, a Tuohy-Borst adapter 56 may be carried on the luer fitting 38 of the guide member. The Tuohy-Borst adapter 56 may be tightened down about the guidewire to lock it securely in place with respect to the guide member 12. The physician then may hold the guide member 12 and guidewire 14 stationary relative to each other (by tightening the Tuohy-Borst adapter 56) while he advances the catheter 10 through the guide member 12. As the catheter passes through the guide member 12, it is caused to wrap about the guidewire as described above so that as the catheter is advanced through the patient's blood vessels, it will enclose the guidewire at all times and fully along the indwelling length of the catheter. At the same time, the proximal end of the guidewire 14 always is exposed so that the physician may manipulate it as desired. When the catheter is advanced to the intended location (which may be monitored fluoroscopically) in the patient's blood vessels, the physician will perform the procedure for which the catheter is designed. In the illustrative embodiment of the invention illustrated in FIG. 1, the procedure would be a dilation procedure to enlarge a stenosed lumen of the blood vessel.

Should the physician have a need to exchange catheters, he may do so by holding the guide member 12 and the protruding proximal end of the guidewire 14 and withdrawing the indwelling catheter. As the catheter is drawn proximally through the guide member 12, the flaps are caused to separate as they are drawn past the distal end 50 of tube 48 and spreader 54. As the distal end of the catheter approaches the guide member 12, both the guide member and catheter are slipped off the proximal end of the guidewire. Another catheter fitted with a guide member 12 then may be placed on the guidewire and advanced along the guidewire and into the patient's blood vessels as was done with the original catheter. Except for the protruding distal end 16, guidewire 14 is contained completely within the indwelling portion of the catheter while the proximal end of the guidewire remains exposed so that it may be controlled from its proximal end by the physician.

Should it be desired to change guidewires while a catheter is present in the patient's blood vessel, that may be done easily by simply withdrawing the guidewire and replacing it with another. During the withdrawal and the replacement, the guidewires will be enclosed within the guidewire lumen 26 of the catheter 10.

It should be understood that although the invention is described, for purposes of illustration as being used in connection with a balloon dilation catheter, the invention is not limited to practice with that type of catheter and may be used with any type of catheter, lead or the like which may be placed in a patient by the use of a guidewire. For example, FIG. 11 illustrates a catheter which is free of encircling members at its distal end. In such a catheter, the slit 28 may extend fully to the distal tip of the catheter. Such a catheter need not be prefitted with a guide member because the distal end of the catheter can be inserted directly into the proximal end of the catheter passageway 46 in the guide member 12. For example, the catheter may be a single lumen low pressure infusion catheter (FIG. 11) or a multiple lumen catheter (FIG. 12) in which the guidewire lumen may be used for low pressure fluid communications while a second unslit lumen may be used for higher pressure fluid communications, such as injection of contrast media, pressure monitoring or the like.

It should be understood that the foregoing description of the invention is intended merely to be illustrative thereof and that other embodiments and modifications of the invention may be apparent to those skilled in the art without departing from its spirit.

Having thus described the invention, what I desire to claim and secure by letters patent is:

1. A catheter comprising:
    an elongate flexible shaft having proximal and distal ends and at least one longitudinally extending lumen open at the distal end of the shaft;
    a connector fitting mounted to the proximal end of the shaft;
    a single, linear longitudinally extending slit formed in the catheter shaft and extending from a location distal of but adjacent to said fitting along the catheter shaft and in communication with the lumen to enable transverse access to the lumen through the shaft, the slit extending along a major portion of the length of the catheter shaft.

2. A catheter as defined in claim 1 wherein the slit terminates at the distal tip of the catheter.

3. A catheter as defined in claim 1 wherein the slit has a distal terminal end proximal of the distal end of the catheter thereby defining an unslit distal segment of the catheter.

4. A catheter as defined in claim 3 further comprising an encircling member mounted to the catheter on the distal segment.

5. A catheter as defined in claim 3 further comprising, in combination:
    means for guiding the guidewire transversely into and out of the lumen through the slit.

6. An apparatus as defined in claim 1 further comprising:
    a guide member mounted on the catheter and having a means for receiving a guidewire and means for merging the guidewire and the catheter by guiding the guidewire transversely through the slit in the catheter and into the guidewire lumen and for separating the guidewire and catheter by guiding the guidewire transversely out of the lumen through said slit.

7. An apparatus as defined in claim 6 wherein the guidewire is disposed within the lumen distally of the guide means and extends transversely out of the lumen and catheter proximally of the guide means.

8. An apparatus as defined in claim 6 wherein said guide means is constructed and arranged to effect such merging and separating in response to relative movement of the guide member to at least one of the guidewire or catheter.

9. A catheter comprising:
    an elongate flexible shaft having proximal and distal ends and at least one longitudinally extending lumen open at the distal end of the shaft;
    a connector fitting mounted to the proximal end of the shaft;
    a longitudinal slit formed in the catheter shaft from a location distal of but adjacent to the proximal fitting and extending in a distal direction along and in communication with the lumen to enable transverse access to the lumen through the shaft, the slit extending along a major portion of the length of the shaft;
    the slit having a distal terminal end proximal of the distal end of the shaft thereby defining an unslit distal segment of the shaft; and
    an encircling member mounted to the catheter shaft on the distal segment, the encircling member comprising a balloon, the catheter having a second lumen extending through the shaft for inflation and deflation of the balloon.

10. A catheter as defined in claims 1, 3 or 9 further comprising:
    a guidewire extending through the slit into and through the slit lumen, and out the distal end of the catheter.

11. A catheter as defined in claim 9 further comprising:
    a proximal fitting connected to the proximal end of the catheter and in communication with the second lumen.

12. A catheter comprising:
    an elongate flexible shaft having proximal and distal ends and at least one longitudinally extending lumen open at the distal end of the catheter;
    a single, linear, longitudinally extending slit formed in the catheter shaft and extending along and in communication with the lumen to enable transverse axis to the lumen through the shaft;
    the slit having a distal terminal end proximal of the distal end of the catheter thereby defining an unslit distal segment of the catheter;
    means for guiding the guidewire transversely into and out of the lumen through the slit, said guiding means comprising:
    a guide member having separate means for receiving the guidewire and the catheter and means for merging the guidewire and the catheter by guiding the guidewire transversely through the slit in the catheter and into the guidewire lumen and for separating the guidewire and catheter by guiding the guidewire out of the lumen transversely through said slit.

13. An apparatus as defined in claim 12 wherein the guidewire is disposed within the lumen distally of the guide means and extends transversely out of the lumen and catheter proximally of the guide means.

14. An apparatus as defined in claim 12 wherein said guide means is constructed and arranged to effect said merging and separating in response to relative movement of the guide member to at least one of the guidewire or the catheter.

15. An apparatus as defined in claim 14 wherein said guide member comprises:
   a body having a guidewire passageway extending therethrough and a catheter passageway which intersects the guidewire passageway, said catheter passageway and guidewire passageway merging into a common passageway.

16. An apparatus as defined in claim 15 further comprising means adjacent the intersection of said passageways for spreading the slit of the catheter.

17. An apparatus as defined in claim 16 wherein the spreading means comprises a spreader member mounted within the body of the guide member at said intersection and being adapted to project through the slit in the catheter into the lumen to spread the edges of the slit.

18. An apparatus as defined in claim 17 wherein the spreader is located at the distal end of the catheter passageway.

19. A catheter comprising:
   an elongate flexible shaft having proximal and distal ends and at least one longitudinally extending lumen open at the distal end of the catheter;
   a single, linear longitudinally extending slit formed in the catheter shaft and extending along and in communication with the lumen to enable transverse access to the lumen through the shaft;
   a guide member mounted on the catheter and having a means for receiving a guidewire and means for merging the guidewire and the catheter by guiding the guidewire transversely through the slit in the catheter and into the guidewire lumen and for separating the guidewire and catheter by guiding the guidewire transversely out of the lumen through said slit;
   said guide member being constructed and arranged to effect such merging and separating in response to relative movement of the guide member to at least one of the guidewire or catheter, said guide member comprising:
   a body having a guide wire passageway extending therethrough and a catheter passageway which intersects the guidewire passageway, the catheter passageway and guidewire passageway merging into a common passageway.

20. An apparatus as defined in claim 19 further comprising means adjacent the intersection of said passageways for spreading the slit of the catheter.

21. An apparatus as defined in claim 20 wherein the spreading means comprises a spreader member mounted within the body of the guide member at said intersection and being adapted to project through the slit in the catheter into the lumen to spread the edges of the slit.

22. An apparatus as defined in claim 21 wherein the spreader is located at the distal end of the catheter passageway.

23. An apparatus as defined in claims 16 or 22 further comprising:
   a tubular member mounted in the guide member adjacent the intersection of the passageways and having a distal end extending toward the common passageway, the tubular member being smaller in diameter than the common passageway to enable the guidewire lumen of the catheter to wrap about the tubular member, the tubular member being disposed to receive and guide the guidewire into the guidewire lumen of the catheter.

24. A method for placing a catheter in a patient comprising:
   providing a catheter having an elongated flexible shaft with a proximal end and a distal end and at least one longitudinally extending lumen open at the distal end of the shaft, a connector fitting mounted to the proximal end of the shaft and a single, linear longitudinally extending slit formed in the catheter shaft and extending from a location distal of but adjacent to said fitting along the catheter shaft and in communication with the lumen to enable transverse access to the lumen through the shaft, the slit extending along a major portion of the length of the catheter shaft;
   placing a guidewire in the patient;
   advancing the catheter over the guidewire while urging the guidewire transversely into the lumen through the slit.

25. A method as defined in claim 24 further comprising:
   removing the catheter by withdrawing the catheter proximally over the guidewire and separating the guidewire and catheter by withdrawing the guidewire transversely through the slit.

26. A method as defined in claim 25 further comprising:
   thereafter providing another such catheter and;
   advancing said another catheter over the guidewire while urging the guidewire transversely into the lumen through the slit.

27. A method as defined in claim 24 further comprising:
   effecting a guidewire exchange by removing the guidewire and inserting another guidewire into the catheter through the slit.

* * * * *